United States Patent [19]

Stavrianopoulos et al.

[11] Patent Number: 4,868,103

[45] Date of Patent: Sep. 19, 1989

[54] ANALYTE DETECTION BY MEANS OF ENERGY TRANSFER

[75] Inventors: Jannis Stavrianopoulos; Elazar Rabbani; Samuel B. Abrams, all of New York; James G. Wetmur, Scardsdale, all of N.Y.

[73] Assignee: Enzo Biochem, Inc., New York, N.Y.

[21] Appl. No.: 831,250

[22] Filed: Feb. 19, 1986

[51] Int. Cl.[4] .................. C12Q 1/68; C12Q 1/70; G01N 33/566; G01N 33/543

[52] U.S. Cl. ............................... 435/5; 435/6; 435/803; 436/501; 436/518; 436/528; 436/536; 436/537; 436/800; 436/805; 436/821; 935/78

[58] Field of Search ............... 436/501, 821, 800, 518, 436/536, 537, 528, 805; 935/78; 435/6, 803, 5

[56] References Cited

U.S. PATENT DOCUMENTS

| | | | |
|---|---|---|---|
| 4,374,120 | 2/1983 | Soini et al. | 435/35 X |
| 4,551,435 | 11/1985 | Liberti et al. | 436/821 X |
| 4,563,417 | 1/1986 | Albarella et al. | 935/77 X |
| 4,568,649 | 2/1986 | Bertoglio-Matte | 436/534 |

FOREIGN PATENT DOCUMENTS 0070685 1/1983 European Pat. Off. .
0144914 6/1985 European Pat. Off. .

OTHER PUBLICATIONS

Norden, et al. Biopolymers, vol. 21, 1713–1734 (1982).
Gutman, et al. The Journal of Biological Chemistry vol. 258, pp. 12132–12134, Oct. 25, 1983.
Thomas, et al. Proc. Natl. Acad. Sci. U.S.A. vol. 75, pp. 5746–5750, Dec. 1978.

*Primary Examiner*—Johnnie R. Brown
*Assistant Examiner*—Jeremy M. Jay
*Attorney, Agent, or Firm*—Serle I. Mosoff; Helen Tzagoloff

[57] ABSTRACT

A method is disclosed to detect the presence of an analyte. The method involves forming a complex comprising the analyte and a binding entity. The binding entity comprises a first partner of an energy transfer system. The complex is then contacted with a reporting entity to form a unit. The reporting entity comprises a second partner of the energy transfer system. The first partner and the second partner are within Furster's radius of each other in the formed unit. The unit is irradiated with energy which can only be absorbed by one of said partners, namely, the energy donor, which then emits fluorescent energy. Some of this energy is absorbed by the other of said partners, namely, the energy acceptor, which also emits fluorescent energy. However, the fluorescent energy of the energy acceptor is of longer wavelength and in addition may be of substantially greater duration than the fluorescent energy of the energy donor. The detection of fluorescence at the longer wavelength or after a given time interval verifies the presence of the analyte.

34 Claims, 2 Drawing Sheets

ANALYTE DETECTION BY MEANS OF ENERGY TRANSFER

BACKGROUND OF THE INVENTION

The present invention relates to a method for determining the presence of an analyte by means of an energy transfer that results in the generation of bathochromic and/or delayed fluorescence emission. Fluorescence radiation, emitted from a first energy emitter ($E_1$), is absorbed by a second energy emitter ($E_2$). This second energy emitter emits fluorescence radiation of a longer wavelength than the first energy emitter. The second energy emitter may in addition emit fluorescence for a substantially longer period than the first energy emitter (in a delayed manner). The detection of either the bathochromic fluorescence or of any fluorescence after a time period during which fluorescence radiation from background sources has decayed verifies the presence of the analyte.

Methods for the in-vitro detection of analytes are well known in the art. The methods include the formation of antibody-antigen complexes (immunodetection), and the formation of nucleic acid complexes (polynucleotide hybridization). The analyte can be an intact cell or a component of the cell. Examples of analytes are bacteria, viruses, antigens, antibodies, and polynucleotides.

The immunoassay for detecting antigen (or antibody) analytes is well established in the art. The assay involves the formation of antigen-antibody complexes. In radio-immunoassay (RIA), a radioactive isotope is used to report the presence of the analyte. In enzyme immunoassay, chromogen or fluorescence generated by means of an enzyme is used to report the presence of the analyte. Several enzyme immunoassays are currently in use. They include the enzyme multiplied immunoassay technique (EMIT) and the enzyme-linked immunosorbent assay (ELISA). The ELISA method comprises the "sandwich" technique for antigen, the antibody assay, and the competitive assay for antigen.

A typical ELISA assay using the sandwich technique is carried out by adsorbing an antibody to the surface of a support. The test specimen is added to the support and the antigen allowed to complex to the antibody. Unbound antigen is washed away. An enzyme-conjugated antibody is added and allowed to react with a different set of determinants on the bound antigen which are not blocked by the support-absorbed antibody. After the reaction, the excess of unbound enzyme-linked antibody is washed away and a substrate of the enzyme is added to the support. The generation of a colored product indicates the presence of the antigen in the test specimen. See Enzyme Immunoassays by S. Bakerman in Laboratory Management, August 1980, p. 21.

A drawback of these methods is that they cannot be carried out in one-step, to achieve detection, i.e., by adding the antibody to the antigen or the antigen to the antibody. One or more washing steps are required to remove antibody unbound to antigen (or vice versa). Also, a number of these methods involves competition kinetics which in some instances can provide ambiguous results.

Polynucleotide hybridization assays using a polynucleotide probe for verifying the presence of a target polynucleotide analyte is a well known method. Hybridization is based on complementary base-pairing.

When single-stranded polynucleotide probes are incubated in solution with single-stranded target polynucleotides that are immobilized on a support, complementary base sequences pair to form double-stranded hybrid molecules. The double-stranded hybrid molecules remain immobilized on the support while unbound polynucleotide probe molecules are washed off. See M. Grunstein and J. Wallis, *METHODS IN ENZYMOLOGY*, volume 68, R.W.U (Ed) (1979) pp. 379–469; A. R. Dunn, and J. Sambrook, *METHODS IN ENZYMOLOGY*, volume 65; part 1, (1980) pp. 468–478; Modified Nucleotides And Methods Of Preparing And Using The Same by D. C. Ward, A. A. Waldrop, and P. R. Langer, European Patent Publication No. 0,063,879 published Nov. 3, 1982; DNA Probes for Infectious Disease by A. J. Berry and J. B. Peter, Diagnostic Medicine (March, 1984) pp. 1–8; and Recombinant DNA Technology: Some Applications In Clinical Microbiology by Wie-Shing Lee and James L. Bennington, Laboratory Management (April, 1985) pp. 21–26.

The polynucleotide probes generally comprise a polynucleotide segment and a signalling segment which is attached to the polynucleotide. The polynucleotide segment of the probe has the ability to base-pair, i.e. hybridize to a sequence of interest, namely the analyte or target polynucleotide. The signalling segment of the probe has or produces the means by which the presence of the analyte moiety can be verified. The means can be, for example, fluorescence, phosphorescence, radioactivity, chromogen, or electron density.

The method of detecting the presence of a target polynucleotide generally involves several steps, one of which is the separation of hybridized polynucleotide probe from unhybridized probe. The separation can be facilitated by immobilizing either the probe or the target onto a solid support. Typically, double-stranded polynucleotides are isolated from a sample suspected of containing a target polynucleotide. The double-stranded polynucleotides are cut into smaller segments by means of restriction endonuclease enzyme digestion, the segments are separated by gel electrophoresis, and the segments are transferred from the gel onto a support, for example, nitrocellulose paper. Alternatively, the double-stranded polynucleotides are fixed directly onto the support without any prior enzyme digestion. The fixed polynucleotides are contacted with a solution containing the polynucleotide probe, and the support is heated to about 80°–90° C. to denature the polynucleotide double-strands. (The double-strands can alternatively be denatured by means of alkali). The system, which now contains the denatured target polynucleotide and the polynucleotide probe, is allowed to cool to an appropriate temperature to allow hybridization to take place. After sufficient time has elapsed for hybridization to be complete, which can be for ten minutes to several hours, the fixed target polynucleotide is washed to remove all unbound polynucleotide probes. The signalling moiety of the polynucleotide probe is now detected, either directly, for example, by means of radioactivity or fluorescence, or indirectly, for example, by means of a chromogen formed through an enzymatic reaction.

A drawback of this method is that it requires several steps before the presence of the target polynucleotide can be verified. Namely, it requires the fixation of the target polynucleotide to a support, the contacting of the target polynucleotide with a polynucleotide probe, and the removal of all unhybridized polynucleotide probes from the support. Besides being time consuming, the method is not readily amenable to automation and requires some expertise for obtaining reproducible results. In addition, hybridization and detection of the target polynucleotide in a one phase system is not possible.

One method seeking to overcome the above drawbacks by detecting the presence of a target polynucleotide with a homogenous (one-step or one phase) nucleic acid hybridization assay has been reported. The method comprises hybridizing first and second single-stranded polynucleotides, both of which contain light-sensitive labels, with a complementary single-stranded polynucleotide target from a sample such that non-radiative energy transfer occurs between the light-sensitive labels of the first and second polynucleotides. At least one of the light-sensitive labels is of the absorber/emitter type such that energy absorbed by this label from the emission of the other light-sensitive label is reemitted at a different wavelength. These secondary emissions can only occur if hybridization of both the first and second single-stranded polynucleotides to the target polynucleotide has taken place. The quantity of the target polynucleotides in the sample is related to the amount of secondary light emitted. See European Patent Publication No. 0,070,685 by Michael James Heller, published Jan. 26, 1983.

A drawback of this method is that it requires two separate polynucleotide strands to detect the presence of a target polynucleotide. In addition, the method requires the presence of a chemiluminescent catalyst, an absorber/emitter moiety, and chemiluminescent reagents effective for causing light emission in the presence of the chemiluminescent catalyst. Furthermore, only one label can be attached per polynucleotide probe because the light-sensitive label is attached to the sugar moiety of a terminal nucleoside. Also, the bulky labels may prevent hybridization of the bases adjacent to the labels.

Another method for detecting the presence of a target polynucleotide by means of a homogeneous assay has been recently reported. The method involves forming a hybrid between the target polynucleotide and the polynucleotide probe, wherein the hybrid has binding sites for two specific binding reagents, one of which comprises a first label and the other a second label. The interaction of the first and second labels provide a detectable response which is measurably different when the two labeled reagents are both bound to the same hybrid, as compared to when the two labeled reagents are not so bound. The formation of the hybrid assay product brings the two labels within approximate interaction distance of one another, e.g., as in the cases of sequential catalyst (enzyme) interaction and energy transfer. Since the labels provide a response which is distinguishable when the labels are associated with a hybridized probe, no separation step is required. See European Patent Application No. 0,144,914 by James P. Albarella et al., published Nov. 29, 1984.

The method has two main embodiments. The first embodiment involves the generation of a component which subsequently produces a color. This embodiment has a drawback in that it requires the use of two distinct chemical reactions, namely, the reaction of the first label to produce a diffusible mediator product, and the reaction of the mediator product with the second label to yield a detectable product. In addition, detection depends on the formation and maintenance of a higher localized concentration of the mediator product in the vicinity of the first label as compared to elsewhere in the solution. Furthermore, both reactions require the use of bulky enzyme molecules attached to the polynucleotide probe. These bulky molecules may sterically "clash" with each other.

A second embodiment involves that of energy transfer, namely the emission of photons from a first label, for example, fluorescence, followed by absorption of the photons by a second label, to either quench the emission, or to provide a second emission. This has a drawback in that when an intercalator is the first label, it is attached to the polynucleotide probe covalently. In addition, the method requires the formation of two complexes, namely the formation of a polynucleotide/polynucleotide complex, and the formation of an antigen/antibody complex. Furthermore, one aspect involves the quenching of emitted photons, and since hybridization of probe to target is usually no more than a few percent, such minute quenching would produce ambiguous results.

Fluorescence detection is widely used in hybridization assays. In fluorescence spectroscopy the substance to be determined which is present in a liquid or a solid phase is subjected to a radiation with a known spectral distribution, for instance light with a limited band width. The fluorescent radiation thereby emitted has a longer wavelength than the exciting radiation and this radiation is specific for the substance to be determined. The measurement of the intensity of the fluorescent radiation constitutes a quantification of the substance to be determined. Fluorescent moieties attached to polynucleotide probes are most efficient when they have a high intensity, a relatively long emission wavelength (more than 500 nm), a high Stoke's shift, and the ability to be bound covalently to a polynucleotide probe without negatively affecting its hybridization capabilities. Aromatic agents used in biological systems that give a rather strong fluorescence and are relatively stable include, for example, fluorescenisothiocyanate (FITC), rhodamines (RBITC, TRITC, RB-200-SC), dansil chloride (DNS-Cl), and fluorescamine (FL).

Fluorescence is generally measured with a spectrofluorimeter. A disadvantage of current methods for detecting signalling moieties with spectrofluorimeters is that the detection sensitivity is limited because of interfering fluorescence or noise in the exciting and detecting systems that increases the background. Interfering fluorescence is generated from substances such as substrate molecules, non-specifically bound compounds, sample holders, air particles, and the intrinsic fluorescence of the biological systems. The background is also affected by a heavy scattering which gives rise to an interference, especially when aromatic organic agents with a small Stoke's shift (less than 50 nm) are used.

Several approaches have been described that attempt to overcome the background problem with fluorescence detection. One approach, described in U.S. Pat. No. 4,058,732, measures delayed fluorescence using a signalling moiety comprising a substance with a fluorescence emission having a duration that considerably exceeds the duration of the fluorescence of the noise sources. A laser pulse is used to excite a sample, and the detection of the fluorescence from the signalling moiety takes place only when a sufficiently long time has passed for the fluorescence from the noise sources to have decayed. This method has drawbacks in that it is not readily adaptable to commercial use, and is not amenable for a homogenous assay.

A second approach, described in U.S. Pat. No. 4,374,120, by E. Soini and I. Hemmilia, discloses a method for determining the presence of an antigen by attaching a first ligand to an antibody, complexing a lanthanide metal to the first ligand, and complexing a second ligand to the lanthanide metal. The antigen-containing sample is fixed to a support, antibodies are then contacted with the sample, and unbound antibodies are washed away. A radiation pulse of short duration is used to excite the second ligand. Energy is transfered from the triplet state of this ligand to the chelated metal which emits radiation at a longer wavelength and for a longer time period than the noise sources. Detection of this delayed fluorescence verifies the presence of the antigen. This method has a drawback in that it cannot be carried out in one step; all unbound antibodies must be washed away from the support.

BRIEF SUMMARY OF THE INVENTION

It is an object of this invention to provide a method for detecting an analyte by complexing it to a binding entity comprising a first partner of an energy transfer system, wherein the formation of the complex induces or allows for the localization of a reporting entity comprising a second partner of the energy transfer system within a proximate distance of the first partner so that energy emitted by one partner, the energy donor or $E_1$, can be absorbed by the other partner, the energy acceptor or $E_2$, and wherein, the fluorescent energy emitted by the second partner is of longer wavelength than that emitted by the first partner and in addition may have fluorescence of substantially greater duration than the first partner or of the background fluorescence.

It is another object of this invention to provide a method for detecting an analyte by complexing it to a binding entity comprising a first energy emitter ($E_1$), wherein the formation of the complex induces or allows for the localization of a reporting entity comprising a second energy emitter ($E_2$) within a proximate distance of $E_1$ so that energy emitted by $E_1$ can be absorbed by $E_2$, and wherein, the fluorescent energy emitted by $E_2$ is of longer wavelength than that emitted by the $E_1$ and in addition may have fluorescence of substantially greater duration than $E_1$ or background fluorescence.

It is an additional object of this invention to provide a method for detecting an analyte by complexing it to a binding entity comprising a second energy emitter ($E_2$), wherein the formation of the complex induces or allows for the localization of a reporting entity comprising a first energy emitter ($E_1$) within a proximate distance of $E_2$ so that energy emitted by $E_1$ can be absorbed by $E_2$, and wherein, the fluorescent energy emitted by $E_2$ is of longer wavelength than that emitted by the $E_1$ and in addition may have fluorescence of substantially greater duration than $E_1$ or background fluorescence.

It is another object of this invention to provide a method for detecting the presence of an antigen in solution by complexing it to a specific antibody comprising an $E_2$ (or $E_1$), contacting the formed complex with Clq (of complement) comprising an $E_1$ (or $E_2$) or a second antibody comprising an $E_1$ (or $E_2$) to form a unit, irradiating the $E_1$ with appropriate energy, and measuring the fluorescence emission.

It is a further object of this invention to provide a method for detecting the presence of an antigen by fixing the antigen to a support, contacting the antigen with a solution containing a specific antibody comprising an $E_2$ (or $E_1$) to form an antigen/antibody complex, contacting said complex with Clq comprising an $E_1$ (or $E_2$) or a second antibody comprising an $E_1$ (or $E_2$) to form an entity, irradiating the $E_1$ with appropriate energy, and measuring the fluorescence emission.

It is an additional object of this invention to provide a method for detecting the presence of an antigen in solution by fixing a specific antibody comprising an $E_2$ (or $E_1$) to a support, contacting the antibody with a solution containing the antigen to form an antigen/antibody complex, contacting said complex with Clq comprising an $E_1$ (or $E_2$) or a second antibody comprising an $E_1$ (or $E_2$) to form an entity, and measuring the fluorescence emission.

It is also an object of this invention to provide a method for detecting the presence of an antigen by fixing the antigen to a support which has attached to it the $E_1$ (or $E_2$), contacting the support with a solution containing an antibody comprising an $E_2$ (or $E_1$), allowing the antibody to complex with the antigen, irradiating the $E_1$ with appropriate energy, and measuring the fluorescence emission.

It is a further object of this invention to provide a method for detecting the presence of a target polynucleotide in solution by hybridizing it to a polynucleotide probe comprising an $E_2$, permitting an $E_1$ to intercalate into the formed hybrid, irradiating the $E_1$ with appropriate energy, and measuring the fluorescence emission.

It is also an object of this invention to provide a method for detecting the presence of a target polynucleotide by fixing the target polynucleotide to a support, contacting the target polynucleotide with a solution containing a polynucleotide probe comprising an $E_2$ to form a hybrid, permitting an $E_1$ to intercalate into the formed hybrid, irradiating the $E_1$ with appropriate energy, and measuring the fluorescence emission.

It is another object of this invention to provide a method for detecting the presence of a target polynucleotide by fixing a polynucleotide probe comprising an $E_2$ to a support, contacting the polynucleotide probe with a solution containing the target polynucleotide to form a hybrid, permitting an $E_1$ to intercalate into the formed hybrid, irradiating the $E_1$ with appropriate energy, and measuring the fluorescence emission.

It is yet another object of this invention to provide a method for detecting the presence of a target polynucleotide by fixing the target polynucleotide to a support which has attached to it the $E_1$ (or $E_2$), contacting the support with a solution containing a polynucleotide probe comprising an $E_2$ (or $E_1$), allowing the target polynucleotide to hybridize to the polynucleotide probe, irradiating the $E_1$ with appropriate energy, and measuring the fluorescence emission.

It is an additional object of this invention to provide a method for detecting the presence of a target polynucleotide in solution by hybridizing it to a polynucleotide probe comprising a hapten, binding an antibody specific for the hapten or for a specific double-stranded polynucleotide comprising an $E_1$ (or $E_2$) to said hybrid to form a complex, contacting said complex with Clq comprising an $E_2$ (or $E_1$) to form an entity, irradiating the $E_1$ with appropriate energy, and measuring the fluorescence emission.

A method is disclosed herein for detecting the presence of an analyte in a homogeneous or one-step assay. The assay can be carried out either in one phase (liquid) or in two phases (liquid and solid). The method comprises first complexing an analyte with a binding entity. The binding entity and the analyte can both be dissolved in the liquid phase or one of them can be dissolved in the liquid phase and one of them can be fixed to a solid support. A reporting entity which is dissolved in the liquid phase or comprises the solid support, is then brought into contact with the complex to form a unit.

The analyte comprises an antigen, antibody, or polynucleotide. The binding entity comprises a recognition segment and a signalling segment. The recognition segment comprises an antibody, antigen, or polynucleotide. The signalling segment comprises either an $E_1$ (an energy donor) or an $E_2$ (an energy acceptor). The reporting entity comprises an $E_1$ or an $E_2$ depending on what the signalling entity does not comprise. The actual composition of the binding entity and the reporting entity depend on the composition of the analyte and the embodiment used for carrying out the detection.

The $E_1$ and $E_2$ constitute the two partners in the energy transfer system. The $E_1$ or $E_2$ can be either a fluorescent aromatic agent or a lanthanide metal. When the $E_1$ is a fluorescent aromatic agent, then the $E_2$ can be a fluorescent aromatic agent or a lanthanide metal. When the $E_1$ is a lanthanide metal, then the $E_2$ must be a fluorescent aromatic agent.

The $E_1$ always absorbs the initial energy and then emits some of this energy at a wavelength which is absorbed by the $E_2$. The $E_2$ then emits some of this energy as fluorescence of a longer wavelength than the $E_1$ and in addition may emit fluorescence whose duration considerably exceeds the duration of the $E_1$ and of the background fluorescence. The presence of this bathochromic and/or delayed fluorescence emission indicates the presence of the analyte.

DETAILED DESCRIPTION OF THE INVENTION

1. GENERAL DESCRIPTION OF THE INVENTION

Figure 1A:
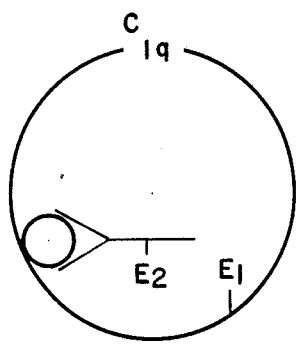
FIG. 1a depicts the detection of an analyte antigen in solution with a binding entity comprising an antibody and the $E_2$ and a reporting entity comprising Clq and the $E_1$.
Figure 1B:
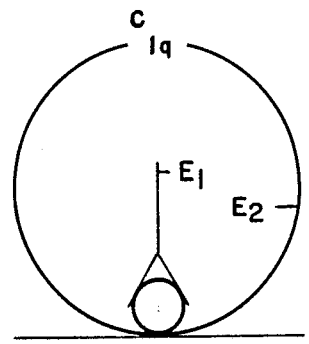
FIG. 1b depicts the detection of an analyte antigen fixed to a solid support with a binding entity comprising an antibody and $E_1$ and a reporting entity comprising Clq and the $E_2$.
Figure 1C:
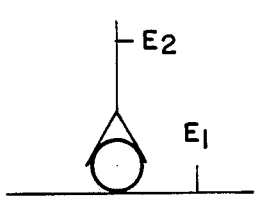
FIG. 1c depicts the detection of an analyte antigen fixed to a solid support with a binding entity comprising an antibody and the $E_2$ and a reporting entity comprising the solid support and the $E_1$.
Figure 1D:
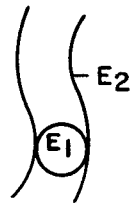
FIG. 1d depicts the detection of an analyte target polynucleotide in solution with a binding entity comprising a complementary polynucleotide and the $E_2$ and a reporting entity comprising an intercalating agent as the $E_1$.
Figure 1E:
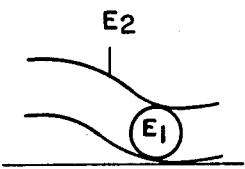
FIG. 1e depicts the detection of an analyte target polynucleotide fixed to a solid support with a binding entity comprising a complementary polynucleotide and the $E_2$ and a reporting entity comprising an intercalating agent and the $E_1$.
Figure 1F:
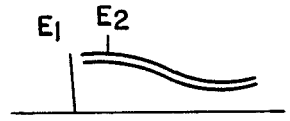
FIG. 1f depicts the detection of an analyte target polynucleotide fixed to a solid support with a binding entity comprising a complementary polynucleotide and the $E_2$ and a reporting entity comprising the solid support and the $E_1$.

This invention discloses homogeneous assay for determining the presence of an analyte. A homogeneous assay, also known as a one-step assay, permits the detection of an analyte upon the contacting of the analyte with a binding entity and a reporting entity (and other components) in an assay medium. There is no need to remove unbound binding entities from the assay medium before detection can be achieved.

The method comprises the use of a first energy emitter, the $E_1$ (energy donor), and a second energy emitter, the $E_2$ (energy acceptor). The $E_2$ is capable of absorbing some of the energy emitted by the $E_1$. The complexing of the binding entity to the analyte causes or allows the reporting entity to contact the formed complex to form a unit. The formation of this unit places the $E_1$ sufficiently proximate to the $E_2$ such that energy emitted by the $E_1$ can be absorbed by the $E_2$. The $E_2$ emits its absorbed energy as fluorescence of a longer wavelength (bathochromic) than the fluorescence of the $E_1$, and in addition, may emit fluorescence of substantially greater duration (delayed) than the $E_1$ (or other background fluorescence). The presence of this bathochromic and/or delayed fluorescence indicates the presence of the analyte.

The method is applicable to the detection of analytes which include, for example, antigens haptens, antibodies, hormones, enzymes, or polynucleotides, and can be carried out in a one phase system i.e. in a solution, or in a two phase system, i.e. in a solution over a solid support. The detection is carried out by forming a complex between the analyte and a binding entity.

The binding entity contains a recognition segment and a signalling segment. The recognition segment is the part of the binding entity that complexes to a part of the analyte. The signalling segment is the part that is involved in the formation of an energy-transfer system to produce a signal indicating that recognition of the analyte by the binding entity has occurred. If the analyte is an antigen, then the binding entity comprises an antibody. If the analyte is an antibody, then the binding entity comprises a antigen. If the analyte is a target polynucleotide, then the binding entity comprises a complementary polynucleotide. The signalling segment comprises either the $E_1$ or the $E_2$. The $E_1$ can be a fluorescent aromatic agent; the $E_2$ can be a fluorescent aromatic agent or a lanthanide metal. The reporting entity comprises either the $E_1$ or the $E_2$. When the signalling segment comprises the $E_1$, then the reporting entity comprises the $E_2$. When the signalling segment comprises the $E_2$, then the reporting entity comprises the $E_1$.

In some embodiments of the assay, all of the components are dissolved in a solution (liquid phase). In other embodiments, one or more of the components are fixed to a solid support while the remaining components are dissolved in a solution. A number of various embodiments are described below. These embodiments are not meant for limitation.

1. The analyte is an antibody and the binding entity comprises an antigen and the $E_1$. The $E_2$ is attached to Clq (of complement) or to an antibody. All the components are dissolved in the liquid phase.

2. The analyte is an antibody and the binding entity comprises an antigen and the $E_2$. The $E_1$ is attached to the Clq or to an antibody. All the components are dissolved in the liquid phase.

3. The analyte is an antigen and the binding entity comprises an antibody and the $E_1$. The $E_2$ is attached to Clq or to an antibody. All the components are dissolved in the liquid phase.

4. The analyte is an antigen and the binding entity comprises an antibody and the $E_2$. The $E_1$ is attached to the Clq or to an antibody. All the components are dissolved in the liquid phase.

5. The analyte is an antibody and is fixed onto a solid support. The binding entity comprises an antigen and the $E_1$. The $E_2$ is attached to Clq or to an antibody. Both the binding entity and the Clq or antibody are dissolved in the liquid phase.

6. The binding entity comprising an antigen and the $E_1$ is fixed onto a solid support. The analyte is an antibody. The $E_2$ is attached to Clq. Both the analyte and the Clq or antibody are dissolved in the liquid phase.

7. The analyte is an antibody and is fixed onto a solid support. The binding entity comprises an antigen and the $E_2$. The $E_1$ is attached to Clq or to an antibody. Both the binding entity and the Clq are dissolved in the liquid phase.

8. The binding entity comprising an antigen and the $E_2$ is fixed onto a solid support. The analyte is an antibody. The $E_1$ is attached to Clq or to an antibody. Both the analyte and the Clq or antibody are dissolved in the liquid phase.

9. The analyte is an antigen and is fixed onto a solid support. The binding entity comprises an antibody and the $E_1$. The $E_2$ is attached to Clq or to an antibody. Both the binding entity and the Clq or antibody are dissolved in the liquid phase.

10. The binding entity comprising an antibody and the $E_1$ is fixed onto a solid support. The analyte is an antigen. The $E_2$ is attached to Clq or to an antibody. Both the analyte and the Clq or antibody are dissolved in the liquid phase.

11. The analyte is an antigen and is fixed onto a solid support. The binding entity comprises an antibody and the $E_2$. The $E_1$ is attached to Clq or to an antibody. Both the binding entity and the Clq or antibody are dissolved in the liquid phase.

12. The binding entity comprising an antibody and the $E_2$ is fixed onto a solid support. The analyte is an antigen. The $E_1$ is attached to Clq or to an antibody Both the analyte and the Clq or antibody are dissolved in the liquid phase.

13. The analyte is an antibody and is fixed onto a solid support. The binding entity comprises an antigen and the $E_1$. The $E_2$ is attached onto the solid support. The binding entity is dissolved in the liquid phase.

14. The analyte is an antibody and is fixed onto a solid support. The binding entity comprises an antigen and the $E_2$. The $E_1$ is attached onto the solid support. The binding entity is dissolved in the liquid phase.

15. The analyte is an antigen and is fixed onto a solid support. The binding entity comprises an antibody and the $E_1$. The $E_2$ is attached onto the solid support. The binding entity is dissolved in the liquid phase.

16. The analyte is an antigen and is fixed onto a solid support. The binding entity comprises an antibody and the $E_2$. The $E_1$ is attached onto the solid support. The binding entity is dissolved in the liquid phase.

17. The analyte is a target polynucleotide and the binding entity comprises a complementary polynucleotide and the $E_2$. The $E_1$ is either an intercalating agent or attached to an intercalating agent. All the components are dissolved in the liquid phase.

18. The analyte is a target polynucleotide and the binding entity comprises a complementary polynucleotide, a hapten attached to the polynucleotide, and an $E_2$ which is attached to an antibody bound to the hapten. The $E_1$ is an intercalating agent or attached to an intercalating agent. All the components are dissolved in the liquid phase.

19. The analyte is a target polynucleotide and is fixed onto a solid support. The binding entity comprises a complementary polynucleotide and the $E_2$. The $E_1$ is an intercalating agent or attached to an intercalating agent. Both the binding entity and the $E_1$ are dissolved in the liquid phase.

20. The binding entity comprising a complementary polynucleotide and the $E_2$ is fixed onto a solid support. The analyte is a target polynucleotide. The $E_1$ is an intercalating agent or attached to an intercalating agent. Both the analyte and the $E_1$ are dissolved in the liquid phase.

21. The analyte is a target polynucleotide and is fixed onto a solid support. The binding entity comprises a complementary polynucleotide, a hapten attached to the polynucleotide, and an $E_2$ which is attached to an antibody bound to the hapten. The $E_1$ is an intercalating agent or attached to an intercalating agent. The binding entity, the antibody, and the $E_1$ are dissolved in the liquid phase.

22. The binding entity comprising a polynucleotide, a hapten attached to the polynucleotide, and a $E_2$ which is attached to an antibody bound to the hapten is fixed onto a solid support. The analyte is a target polynucleotide. The $E_1$ is an intercalating agent or attached to an intercalating agent. The analyte, the antibody, and the $E_1$ are dissolved in the liquid phase.

23. The analyte is a target polynucleotide and is fixed onto a solid support. The binding entity comprises a complementary polynucleotide and the $E_1$. The $E_2$ is fixed onto the solid support. The binding entity is dissolved in the liquid phase.

24. The analyte is a target polynucleotide and is fixed onto a solid support. The binding entity comprises a polynucleotide and the $E_2$. The $E_1$ is fixed onto a solid support. The binding entity is dissolved in the liquid phase.

The method of the assay involves irradiating a fluorescence-emitting agent ($E_1$), generally an aromatic agent, causing some of its electrons to "jump" to an excited state. This agent emits fluorescent energy when its electrons return to the ground state. Some of this energy can be absorbed by a proximate lanthanide metal or another fluorescent aromatic agent ($E_2$), which then emits some of this energy also as fluorescent energy. However, the fluorescent energy of the $E_2$ is emitted at a longer wavelength (bathochromic) than the fluorescence of the $E_1$ and in addition, the fluorescence energy of the $E_2$ may last longer than the fluorescence of the $E_1$ or is "delayed" as compared to that of the $E_1$. Thus, the detection of bathochromic and/or delayed fluorescence indicates the presence of the analyte.

Important limitations are that the radiation energy used to excite the $E_1$ must be absorbed only by the $E_1$ and not by the $E_2$, and that the $E_1$ is brought within the required proximate distance of $E_2$ only if the binding entity is complexed to the analyte. Therefore, the concentrations of the $E_1$ and the $E_2$ should not be of a value that they are placed within the required distance of each other even without the analyte first complexing to the binding entity. The required distance between the $E_1$ and the $E_2$ should not be greater than about the Furster's radius, preferably not more than about 30Å.

By way of illustration, an example of a one phase assay where the analyte is an antigen is the addition of a binding entity comprising an antibody as the recognition segment and a chelator-lanthanide metal complex ($E_2$) as the signalling segment, and a reporting entity comprising Clq and a fluorescent aromatic agent ($E_1$), to a solution comprising the test antigen. The concentration of the $E_1$ and $E_2$ is such that random diffusion of the $E_2$ does not place it sufficiently proximate to the $E_1$ that the $E_2$ can absorb energy emitted by $E_1$. The complexing of the antibody to antigen, however, allows the Clq to bind to the formed complex. This brings the $E_1$ (which is attached to the Clq) within a distance of $E_2$, that energy emitted by the $E_1$ is absorbed by the $E_2$. Irradiation of the $E_1$ with energy of the appropriate wavelength induces the $E_1$ to emit fluorescent energy. Some of this energy is absorbed by the $E_2$ which then emits some of this energy as fluorescent energy of a longer wavelength as compared to the wavelength of the fluorescent energy emitted by the $E_1$ and also in some instances as delayed fluorescent energy. This emitted fluorescence can then be measured. If test antigen was not present in the sample, then no complex comprising antigen and antibody would be formed to which Clq could bind. No $E_1$ would thus become localized proximate to the $E_2$, no energy would be transferred from the $E_1$ to the $E_2$, and accordingly, no fluorescent energy shift or delayed fluorescence would be observed.

An example of a two phase assay where the analyte is an antigen is the addition of a solution containing the binding entity comprising the $E_2$ to a solid support onto which the antigen has been fixed. The $E_1$ is provided in one of two ways. The first way is the addition to the solution of a reporting entity comprising Clq and the $E_1$. The reporting entity binds to the complex to form a unit. The second way is the attachment of the $E_1$ onto the solid support by means of a linker arm. Upon the formation of the antigen/antibody complex on the support to form a unit, the linker arm permits the $E_1$ to be sufficiently proximate to the $E_2$ that an energy transfer can occur. If antigen was not present in the sample, then no complex would be formed, and accordingly, the $E_1$ attached to the support would not be sufficiently proximate to the $E_2$ that an energy transfer from $E_1$ to $E_2$ could occur.

An example of a one phase assay where the analyte is a target polynucleotide is the addition of a binding entity (binding entities for polynucleotides are generally known as polynucleotide probes) comprising a polynucleotide as the recognition segment and a chelator-lanthanide metal complex ($E_2$) as the signalling segment, and a reporting entity comprising a fluorescent aromatic intercalating agent ($E_1$) to a solution comprising the test target polynucleotide. The concentration of the $E_1$ and $E_2$ is such that random diffusion of the $E_2$ doesn't place it sufficiently proximate to the $E_1$ that the $E_2$ can absorb energy emitted by the $E_1$. The hybridization of the polynucleotide probe to the target polynucleotide to produce a target polynucleotide/polynucleotide probe hybrid, however, allows the $E_1$ to intercalate into this hybrid. This intercalation brings the $E_1$ within a distance of $E_2$, that energy emitted by the $E_1$ is absorbed by the $E_2$. Irradiation of the $E_1$ with energy of the appropriate wavelength induces the $E_1$ to emit fluorescent energy. Some of this energy is absorbed by the $E_2$ which then emits some of this energy as fluorescent energy of a longer wavelength and also in some instances as delayed fluorescent energy. If target polynucleotide was not present in the sample, then no hybrid comprising target polynucleotide and polynucleotide probe would be formed into which $E_1$ could intercalate. No $E_1$ would thus become localized proximate to the $E_2$, no energy would be transferred from the $E_1$ to the $E_2$, and accordingly, no fluorescent energy shift or delayed fluorescence would be observed.

An example of a two phase assay where the analyte is a target polynucleotide is the addition of a solution containing the polynucleotide probe comprising the $E_2$ to a solid support onto which the target polynucleotide has been fixed. The $E_1$ is provided in one of two ways. The first way is the addition to the solution of a reporting entity comprising a fluorescent aromatic intercalating agent. The second way is the attachment of a fluorescent aromatic agent onto the solid support by means of a linker arm. The agent need not be an intercalating agent. Upon the formation of the target polynucleotide/polynucleotide probe hybrid on the support, the linker arm permits the $E_1$ to be sufficiently proximate to the $E_2$ that an energy transfer can occur. If target polynucleotide was not present in the sample, then no hybrid would be formed, and accordingly, the $E_1$ attached to the support would not be sufficiently proximate to the $E_2$ that an energy transfer from $E_1$ to $E_2$ could occur.

2. DESCRIPTION OF THE BINDING ENTITY

A. THE BINDING ENTITY COMPRISES AN ANTIGEN OR ANTIBODY

1. THE RECOGNITION SEGMENT

This is the portion of the binding entity which recognizes a structure or shape of a segment of the analyte and thus enables the binding entity to form a complex with the analyte. When the analyte is an antigen then the recognition segment comprises an antibody. When the analyte is an antibody, then the recognition segment comprises an antigen.

The reaction of antibodies (Ab) with antigens (Ag) is a well known and described reaction in the field of immunology. An antigen has two properties: (a) immunogenicity, i.e., the capacity to stimulate the formation of the corresponding antibodies, and (b) the ability to react specifically with these antibodies. Haptens are substances that are not immunogenic but they react selectively with antibodies of the appropriate specificity. They provide antigenic determinants to an antigen molecule. Antibodies are proteins that are formed in response to an antigen and which react specifically with that antigen. All antibodies belong to a special group of serum proteins called immunoglobulins.

The antibody should be specific for at least one antigenic determinant site or epitope on the antigen. The antibody is prepared by exposing immunoglobulins to the antigen. Methods of purifying antibodies are based on the dissociability of antibody/ligand complexes. At least two steps are usually involved: (1) Antibodies are precipitated from the serum with soluble antigens or absorbed by insoluble antigenic materials; (the latter are often prepared by coupling small haptenic groups or soluble proteins to an insoluble matrix, such as agarose); and (2) After the extraneous serum is washed away, the antibodies are eluted from the insoluble complexes by means of specific or nonspecific procedures.

A number of antibodies can be purified by specific procedures. With aggregates whose stability depends largely on specific ionic interactions, such as those involving types 3 and 8 pneumococcal polysaccharides, strong salt solutions (e.g., 1.8M NaCl) elute purified antibodies effectively. When the specific antigenic determinants are simple haptenic groups, such as 2,4-dinitrophenol, small univalent haptens that encompass the crucial part of the determinant (e.g. 2,4-dinitrophenol) are useful for competitive displacement from the precipitating antigen or adsorbent, yielding soluble antibody hapten complexes. Depending upon the properties of the antigen, the adsorbent, and the hapten, diverse procedures are then used to isolate the soluble antibody-hapten complexes and finally to separate the hapten from the antibody (e.g., ion-exchange resins, dialysis, gel filtration). When small univalent haptens are employed for specific elution of antigens it is desirable to use those haptens that are both (1) weakly bound by the antibody and (2) highly soluble. Highly concentrated solutions of hapten can then be used to elute the antibody in high yield, and the weakly bound hapten is easily separated from the soluble hapten-antibody complex, e.g., by dialysis or gel filtration.

Nonspecific procedures are used for the isolation of other antibodies to protein antigens. It is usually necessary to expose specific antigen/antibody aggregates to conditions that cause reversible denaturation of the antibody, allowing it to dissociate from the antigen. Organic acids at pH 2 to 3 are often effective; various procedures are then used to separate the denatured antibody and antigen, depending upon the properties of the antigens. Since antibodies usually regain their native structure on being restored to physiological conditions, neutralization of the antigen-free material yields active antibody, usually without excessive losses due to persistent denaturation.

Though antibodies can be isolated from serum in high yield (50 to 90%) and with high purity (90% of the recovered antibodies usually react specifically with antigen) the purified molecules are usually heterogeneous with respect to affinity and with respect to many other physical and chemical properties.

Antigens generally comprise proteins, polysaccharides, or polynucleotides. A variety of methods are available for purifying antigens. They include chromatography, electrophoreses, centrifugation, and immunodiffusion. These methods are well known to one skilled in the art.

2. THE SIGNALLING SEGMENT

This is a moiety of the binding entity which is involved in the generation of a signal by means of energy transfer. The signal consists either in the emission of bathochromic fluorescence with respect to the $E_1$ or in the emission of delayed fluorescence. The presence of the signal indicates the presence of the analyte.

The signalling segment is attached to the recognition segment. The attachment can be by covalent or noncovalent means. The attachment can also be through a linker arm. The signalling segment comprises either an $E_1$ or an $E_2$. The $E_1$ is generally a fluorescent aromatic agent; the $E_2$ is either a fluorescing aromatic agent or a lanthanide metal. Details of attachment of the signalling segment to the recognition segment are described hereinbelow.

B. THE BINDING ENTITY COMPRISES A POLYNUCLEOTIDE

1. THE RECOGNITION SEGMENT

This is a moiety of the binding entity that recognizes the structure of a target polynucleotide, and comprises a polynucleotide. This type of binding entity is known in the art as a polynucleotide probe. The target polynucleotide complexes with the polynucleotide probe to form a target polynucleotide/polynucleotide probe hybrid.

The polynucleotide portion of the polynucleotide probe comprises at least one single-stranded base sequence substantially complementary to the base sequence to be detected (target polynucleotide). The sequence should comprise at least about twelve bases to impart specificity to the probe. However, such a base sequence need not be a single continuous complementary polynucleotide sequence, but can be comprised of two or more individual complementary sequences interrupted by non-complementary sequences. In addition, the complementary region of the probe can be flanked at the 3'- and 5' termini by non-complementary sequences, such as those comprising the DNA or RNA of a vector into which the homologous sequence had been inserted for propagation. In either instance, the probe as presented as an analytical reagent will exhibit detectable hybridization at one or more points with sample nucleic acids of interest.

Methods for preparing a polynucleotide that is substantially complementary to a target polynucleotide are well known and routine in the art. The most commonly used methods are those of recombinant DNA and cloning. One widely used vector is the M13 phage. Briefly, the method entails (1) cleaving the M13 RF (replicative form) DNA with one of the restriction enzymes having a unique recognition sequence in the cloning region (2) ligating the desired polynucleotide into the cleaved insertion site (3) transforming *E. coli* host cells (4) growing these host cells on nutrient-containing plates and selecting the colorless plaques (5) amplifying the phages from single plaques in small cultures (6) harvesting the phages from culture supernatant and removing the protein coat by treatment with phenol, and (7) precipitating the purified DNA with ethanol. Greater detail can be found in M13 CLONING AND SEQUENCING HANDBOOK Published by Amersham Corporation (1983) and in MOLECULAR CLONING by T. Maniatis, E. F. Fritsch, and J. Sambrook, published by Cold Spring Harbor Laboratory (1982).

Specific polynucleotides can also be prepared with a DNA Synthesizer Instrument such as one manufactured by Applied Biosystems, 850 Lincoln Centre Drive, Foster City, Calif. 94404, using the appropriate nucleotide precursors. According to the manufacturer, one can prepare polynucleotides of about 120-200 bases with great specificity. The synthetic schemes involve the use of phosphoramidites to link together predetermined bases. Other manufacturers of polynucleotide synthesizers include Biosearch Inc., 2980 Kerner Boulevard, San Rafael, Calif. 94901, and Beckman Instruments, 1050 Page Mill Road, Palo Alto, Calif. 94304.

The polynucleotide can also be prepared by the method of nick translation. This method involves removing selected bases from double-stranded polynucleotides and replacing some of them with other predetermined bases. This method however produces a double-stranded probe. Since this invention requires the use of single-stranded probes, as discussed hereinbelow, where only one of the two complementary strands are present during the assay, the two strands of the probe must be separated from each other. This can be achieved by column chromotography using, for example, methylated albumin columns. The separation however depends on the two strands having different ratios of G-C/A-T. Thus, where the G-C content of the probe is about 50%, nick translation cannot be used to prepare the probe.

2. THE SIGNALLING SEGMENT

This is a moiety of the binding entity that is involved in the generation of a signal by means of energy transfer. The signal is the production of bathochromic and/or delayed fluorescence. The signalling segment is attached to the recognition segment of the binding entity. The signalling segment can be attached to the recognition segment directly or through a linker arm. The signalling segment can also be attached to the recognition segment covalently or non-covalently. An example of covalent attachment is where a chelator/metal complex is attached by means of an allylamine to a complementary polynucleotide. The allylamine is the linker arm. An example of non-covalent attachment is where a chelator/metal complex is covalently attached to an antibody, and the antibody is non-covalently bound to a hapten which is covalently attached to the complementary polynucleotide. In this instance, the hapten and antibody comprise the linker arm.

The signalling segment is either an $E_1$ or an $E_2$. The $E_1$ is generally an aromatic fluorescence-emitting agent while the $E_2$ is an aromatic fluorescence-emitting agent or a lanthanide metal. Details of attachment of the signalling segment to the recognition segment are described hereinbelow.

3. POLYNUCLEOTIDE PROBE FORM

A bathochromic and/or delayed fluorescence emission should only occur when the polynucleotide segment of the polynucleotide probe is hybridized with the target polynucleotide. The shift or delay in fluorescence should not occur in the presence of hybrids if not one of the hybrid strands is that of the target polynucleotide. The target polynucleotide to which the polynucleotide portion of the polynucleotide probe hybridizes must be one originating from the sample. Thus, the polynucleotide probe must be provided to the sample single-stranded and none of the provided single-strands should be complementary to each other. If the polynucleotide probe is provided to the sample double-stranded and then denatured in the sample, the signalling segment of the probe will assist in the generation of a shift in fluorescence emission or of delayed fluorescence when one polynucleotide probe strand hybridizes with the complementary probe strand to which it was originally hybridized. This will produce a false positive result.

The formation of hairpin loops can also result in the production of a false positive result when the reporting entity comprises on interelating agent. This can be minimized by using polynucleotide probes not longer than about 30 base sequences, or by carrying out the assay at elevated temperatures or under stringent conditions.

It is preferable that the polynucleotide probe comprise an integral strand. That is, bathochromic and/or delayed fluorescence emission should be generated with the assistance of the signalling segment upon the hybridization of only two strands. This permits the detection of a target polynucleotide with only one polynucleotide probe molecule. However, there may be instances where the polynucleotide probe will comprise two different polynucleotide strands. This can be, for example, where each polynucleotide strand contains different signalling segments and the two polynucleotide strands hybridize to adjacent non-overlapping sequences on the target polynucleotide. The signalling segment of each strand itself does not produce a detectable bathochromic and/or delayed fluorescence, but the interaction of the two signalling segments together, produces a detectable bathochromic and/or delayed fluorescence. Such a situation is contemplated as being covered by this invention.

3. THE REPORTING ENTITY

This is an entity other than the binding entity which comprises one partner of the energy transfer system. The partner can be either the $E_1$ or the $E_2$. The reporting entity and the binding entity together comprise a unit. The unit contains the means for generating an energy transfer system, because one part of the unit comprises the $E_1$ and the other part of the unit comprises the $E_2$. The reporting entity also comprises a component which can be either Clq, an antibody, an aromatic intercalating agent, or a support, depending on the assay. The energy transfer partner of the reporting entity is attached to this component which can be either to Clq or to an antibody, or to an aromatic intercalating agent when the analyte is in solution, and can also be attached to a support when the analyte or binding entity is fixed to a support. The $E_1$ must be brought within the required proximate distance of the $E_2$ only when the binding entity is complexed to the analyte. Thus, the concentrations of the $E_1$ and the $E_2$ should preferably be such that random diffusion does not place significant amounts of the two within a distance that the $E_2$ can absorb energy emitted by the $E_1$. Amounts are considered sifnificant if they greatly increase the background and make accurate measurements difficult.

Clq is one of the complement proteins. Complement (C) is now known to consist of 11 proteins. The proteins make up about 10% of the globulins in normal serum of man and other vertebrates. These proteins are not immunoglobulins (IGA), and they are not increased in concentration by immunization. They react with a wide variety of antibody-antigen (Ab-Ag) complexes, and exert their effects primarily on cell membranes, causing lysis of some cells and functional aberrations in others, e.g., degranulation of mast cells with release of histamine, increased permeability of small blood vessels, directed migration of polymorphonuclear leukocytes, increased phagocytic activity by leukocytes and macrophages, and bacteriolysis. The 11 proteins of complement are Clq, Clr, Cls, and C2–C9. Clq is the recognition unit of the complex. It consists of five subunits, each with one binding site for the heavy chains of those Ig classes (e.g., IgG-1, IgG-2, IgG-3, IgM) that can trigger the entire C sequence. Unlike other C proteins, Clq has stable combining sites and requires no activation. The Clq has a striking chemical similarity to collagen, i.e., it has a high content of glycine, hydroxyproline, and hydroxylysine, with a galactose-glucose disaccharide attached to the hydroxyl of hydroxylysine, and it can be inactivated by collagenase.

The $E_1$ or $E_2$ can be attached to Clq when the analyte is an antigen or antibody. The Clq does not bind either to antigens or to antibodies individually. Only following the complexing of the antigen to the antibody does the Clq bind to the formed complex. Thus, for example, when the assay is carried out in solution, the Clq will bring the $E_1$ (or $E_2$) within the required distance of $E_2$ (or $E_1$) only when the antigen analyte is bound to the antibody binding entity comprising the $E_2$ (or $E_1$). In the presence of analyte, binding entity, and Clq, irradiation of the $E_1$ with appropriate energy will result in a transfer of energy from the $E_1$ to the $E_2$. Methods for attaching an $E_1$ or $E_2$ to Clq are similar to those used for attaching linker arms which are described hereinbelow.

The $E_1$ or $E_2$ can be attached to an antibody when the analyte is an antigen, antibody or polyncleotide. The analyte polynucleotide includes RNA/DNA, RNA/RNA and DNA/DNA hybrids. The antibody would be one that would not bind to either the analyte or binding entity individually. The antibody would only bind to a complex comprising the analyte and the binding entity. The reporting entity would thus comprise an antibody to this complex and an $E_1$ or $E_2$.

The isolation of an antibody that is only specific for a complex is readily achieved by one who is skilled in the art. It involves the isolation of antibodies from animal of an inbred strain, and creating a tolerance in one of these animals for the particular antigen. An antibody can be isolated that is specific only for the analyte/binding entity complex. An $E_1$ or $E_2$ can be attached to the particular antibody by the method described hereinbelow.

The $E_1$ or $E_2$ can be attached to a support when the analyte is an antigen, antibody or polynucleotide. The support can be glass, plastic, cellulose, or a gel matrix (such as sepharose). The $E_1$ or $E_2$ can be attached to the support by means of a linker arm. Some supports may need to be siliconized prior to the attachment of a linker arm.

The $E_1$ can be a fluorescent aromatic intercalating agent that is unattached to any other moiety when the analyte is target polynucleotide. This is when the intercalating agent emits fluorescence at a wavelength which can be absorbed by the $E_2$. However, if the intercalating agent does not emit at a wavelength at which the $E_2$ can absorb, then the $E_1$ can be attached to an aromatic intercalating agent. The $E_1$ can be attached to the intercalating agent by means of a linker arm. The intercalating agent becomes inserted into the hybrid formed from the target polynucleotide (analyte) and the polynucleotide probe (binding entity). This allows the $E_1$ to lie at the periphery of the double helix adjacent to on $E_2$ which is part of the polynucleotide probe. An energy transfer from the $E_1$ to the $E_2$ can then occur. Without prior hybridization, no energy transfer occurs.

4. DESCRIPTION OF LINKER ARM

A. GENERAL DESCRIPTION

The signalling segment is generally attached to the recognition segment of the binding entity by means of a linker arm so that there is minimal steric interference between the signalling and recognition segments of the binding entity, and so that the signalling segment allows the $E_1$ to be within the required distance of $E_2$. The linker arm refers to the fragment in the binding entity attaching the signalling segment to the recognition segment.

B. THE LINKER ARM WHEN THE RECOGNITION SEGMENT COMPRISES AN ANTIBODY OR ANTIGEN

In this embodiment, the linker arm attaches a fluorescent aromatic agent or a chelator-metal complex to either an antibody or an antigen. The linker arm should not be one that interferes, however, with the formation of an antigen/antibody complex.

Antibodies and/or antigens comprise a number of primary and secondary amino and hydroxy functional groups. Some antigens also comprise one or more sulfhydryl groups. The covalent attachment of a linker arm by means of electrophilic addition to most of these functionalities would not significantly intereefere with the formation of an antibody/antigen complex since the active site of the antibody comprises, relatively speaking, only a few of these atoms. Functional groups by which a linker arm can be attached to an antibody or antigen and other characteristics of the linker arm are described hereinbelow in section C.

C. THE LINKER ARM WHEN THE RECOGNITION SEGMENT COMPRISES A POLYNUCLEOTIDE

In this embodiment, the linker arm attaches a fluorescent aromatic agent or a chelator-metal complex to a polynucleotide. The linker arm should be one that does not substantially interfere with the hybridization of the polynucleotide probe to the target polynucleotide. Therefore, the linker arm and/or chelator: (a) should not prevent the base to which it is attached from pairing with its complementary base; (b) should not prevent the complexing of the complementary bases, so as to prevent the hybridization of the polynucleotide probe to the target polynucleotide; (c) should not prevent the incorporation of nucleotides to which the linker arm is attached by the polymerase enzymes (unless it is at a terminal position of the polynucleotide sequence); and (d) preferably, should not change the conformation of the sugar moieties in the polynucleotide.

The linker arm is generally attached covalently to the polynucleotide, but can also comprise non-covalently attached moieties. The attachment is preferably to the base moiety, although it can be to the sugar moiety, or the phosphate moiety. The base moiety can be either a purine or a pyrimidine. As mentioned hereinabove, the attachment of the linker arm to the base moiety should preferably be to a position at which the linker arm does not interfere with Watson-Crick pairing of the bases. Suitable positions are, for example, positions 5 and 6 of uracil, positions 5,6, and the exocylic 4-amino of cytosine, positions 7 and 8 of deazapurine, position 8 of guanine, and positions 8 and the exocyclic 6-amino of adenine. A preferred linker arm for attachment to the base moiety is allylamine. See European Patent Publication No. 0,063,879 by David Ward et al., published Nov. 3, 1982 which is hereby incorporated by reference.

Preferred positions on bases are the 5 and 6 positions of pyrimidines and the 7 position on deazapurines, since 8-purine nucleotides are poor substrates for the polymerase enzymes, and the exocyclic amino group of either adenine or cytosine is involved in base-pairing to thymine and uracil, or to guanine respectively. Although a substituent at an exocyclic amino group of a base does not prevent that base from pairing to its complementary base in some instances, the substituent may alter the optimum orientation between the two bases. Preferred pyrimidines are uracil and cytosine, with 5 being the preferred position. Preferred purines are deazaadenine and deazaguanine.

D. METHODS FOR ATTACHING A LINKER ARM

In the instance when the recognition segment is an antigen, any condition which does not result in the modification or blocking of required epitopes is satisfactory. In the instance when the recognition segment is an antibody, any condition which does not denature the antibody or result in the modification of the active site is satisfactory. In the instance when the recognition segment is a polynucleotide, any condition which does not result in the modification or blocking of the functional groups of the bases required for hybridization or the cleavage of the base from the sugar is satisfactory. The optimum conditions including those of pH, temperature, solvent, or reaction time can readily be determind by one skilled in the art.

The linker arm comprises the group of atoms joining the recognition segment to the chelator-metal complex or to the fluorescent aromatic agent. The linker arm can be joined to the recognition segment by any number of methods. The linker arm must have a first functional group by means of which it can be attached to the recognition segment, and a second functional group by means of which it can be attached to the chelator-metal complex or fluorescent aromatic agent. The linker arm can be attached by means of a carbon-carbon single bond, carbon-carbon double bond, carbon-nitrogen single bond, carbon-nitrogen double bond, carbon-oxygen single bond, carbon-sulfur single bond, or carbon-silicon single bond. Suitable functional groups include but are not limited to amino groups, thio groups, aklyl sulfates, and halides.

It is not necessary that the linker arm be attached to the recognition segement as one fragment. The linker arm can be constructed by attaching a first fragment to the recognition segment, followed by the attachment of a second fragment to the first fragment. Examples of suitable first fragments are: —CH=CH—CH$_2$—NH—; —CH=CH—CH$_2$—CH$_2$—SH; and —CH=CH—CH$_2$—O—CH$_2$—CH$_2$—NH Examples of suitable second fragments are:

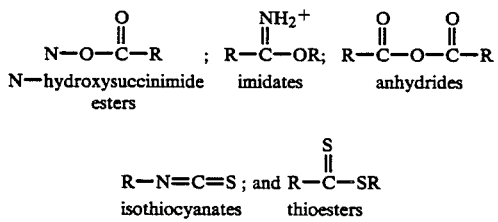

N—hydroxysuccinimide esters ; imidates ; anhydrides

R—N=C=S ; and R—C(=S)—SR isothiocyanates ; thioesters

General methods for attaching a linker arm onto a base of a polynucleotide are discussed in J. L. Ruth and D. E. Bergstrom, J. Org. Chem., 43, 2870, (1978); D. E. Bergstrom and M. K. Ogawa, J. Amer. Chem. Soc. 100, 8106, (1978); and C. F. Bigge, P. Kalaritis, J. R. Deck, and M. P. Mertes, J. Amer. Chem. Soc. 102, 2033 (1980). One preferred method is the one disclosed in detail in European Patent Application No. 0,063,879, by David C. Ward, et al., published in Nov. 3, 1982, which is hereby incorporated by reference. The method involves reacting a linker arm or a linker arm fragment containing an alpha vinyl group with a mercurated base in the presence of K$_2$PdCl$_4$, wherein the mercury is bound as Hg$^+$ to the position of the base which is to react with the linker arm. The scheme is shown below.

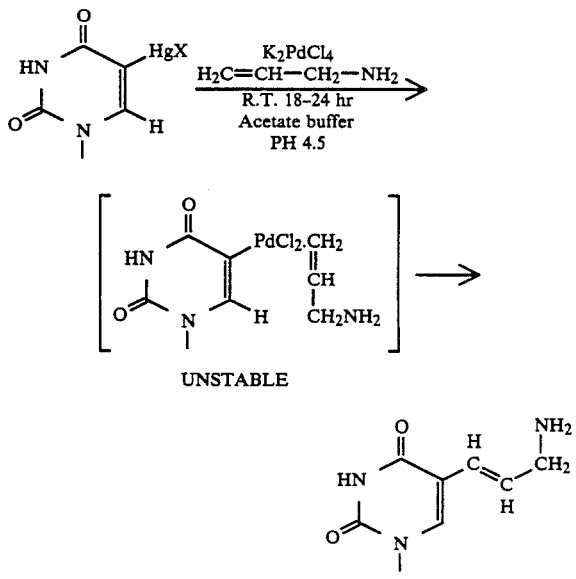

There are no particular size or content limitations for the linker arm. The linker arm can contain from about two carbons to about any number of carbons, as long as the chelator is within the required distance from the recognition segment. The linker arm can contain heteroatoms and unsaturations. The linker arm can comprise aliphatic, alicyclic or aromatic moieties. The actual size or content of the linker arm will depend on the recognition segment to which it is attached and on the chelator-metal complex or fluorescent-aromatic agent chosen.

Attachment of the linker arm to the sugar moiety of a polynucleotide can be my means of a Schiff base to the 1' aldehyde following depurination or depyrimidation of preselected bases, or it can be to the 2' hydroxy in the case when the sugar is ribose. The linker arm when attached to the 1' aldehyde can comprise, for example, an amine, hydrazine, or hydrazide functionality. Such a method is disclosed in pending U.S. patent application Ser. No. 06/765,288 by Jannis Stavrianopoulos, filed on Aug. 13, 1985, and assigned to the same assignee which is hereby incorporated by reference. Attachment of a linker arm to the phosphate moiety can be by alkylation of the phosphate moiety. See U.S. Pat. No. 4,469,863 by P.O.P.Ts'O and P. S. Miller which is hereby incorporated by reference.

When the linker arm is attached to the base moiety, it is preferable to attach it to the base at the nucleoside or nucleotide level. This is because the reaction conditions that may be required to attach the linker arm to the base may cause undesirable side reactions to a polynucleotide. Furthermore, attachment at the polynucleotide level may give inconsistent and irreproducible yields. Attachment at the nucleoside or nucleotide level permits the modified nucleoside or nucleotide to first be purified, and then to be incorporated into a polynucleotide. The incorporation can be either by cloning, for example, in an M13 vector, or by synthesis with a polynucleotide synthesizer instrument as disclosed hereinabove.

For incorporation by an M13 vector, the modified nucleotide must be a relatively efficient substrate for the commonly studied nucleic acid polymerases. Thus, the linker arm should not sterically interfere either with the active site on the enzyme or with the complementary base-pairing of the modified nucleotide. Substitution at positions that alter normal "anti" nucleoside conformation should also be avoided since such conformational changes usually render the modified nucleotide a poor substrate for the polymerase enzymes.

When the linker arm is attached to the 1' aldehyde of the sugar, the linker arm must be attached following the formation of the polynucleotide portion of the polynucleotide probe. This is because attachment of the sugar requires a free aldehyde at the 1-position of the sugar. The free aldehyde is formed by depurination or depyrimidation. A moiety comprising a sugar and phosphate without a base is not a substrate for the polymerase enzymes. Thus, the linker arm must be attached by first selectively depurinating or depyrimidating the desired polynucleotide sequence, and then attaching the linker arm, to the sugar by means of the aldehyde. When the linker arm is attached to the 2 hydroxy of a ribose sugar, the linker arm can be attached at the nucleoside, nucleotide or polynucleotide level. This is because nucleotides modified by a linker arm can be incorporated into a polynucleotide by means of a gene synthesizer instrument. When the linker arm is attached to the phosphate, the linker arm must be attached at the nucleoside or nucleotide level so that the attachment is not at positions other than at the phosphate.

5. ATTACHMENT OF THE CHELATOR

A chelator is a moiety which can sequester and bind a metallic cation. The chelator has two or more functional groups which interact non-covalently with the metal. The chelator can be attached to an antigen, antibody, polynucleotide or support. The attachment of chelator-metal groups to antibodies is known in the art. See U.S. Pat. No. 4,374,120 by E. Soini and I. Hemmilia which is hereby incorporated by reference. The attachment of metal-chelating groups to polynucleotides is also known in the art. See European Patent publications: No. 97,373 by D. Engelhardt et. al., published on Jan. 4, 1984; No. 150,844 by J. Stavrianoupoulos, published on Aug. 7, 1985; and No. 157,788 by J. Stavrianoupoulos, published on Sept. 18, 1985, which are coassigned to the same assignee of this patent application, which are hereby incorporated by reference.

Examples of chelators, not meant for limitation, are ethylenediaminetetraacetic acid (EDTA) which can be derived from 1-(p-benzenediazonium) EDTA (I);

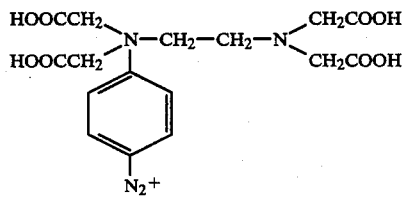

diethylenetriaminepentaacetic acid (DTPA) II;

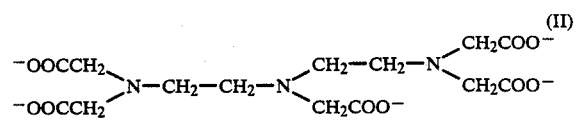

and trans-diaminocylohexanetetraacetic acid (DCTA) III.

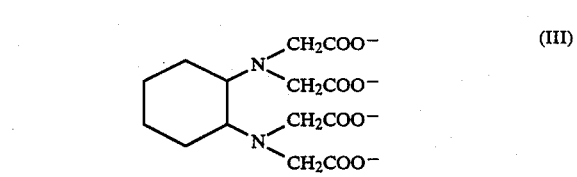

Other chelators are listed in "Diffusion-Enhanced Fluorescene Energy" by L. Stryer, D. D. Thomas, and C. F. Meares, Ann. Rer. Biophys. Bioeng. (1982), 11:203–32, which is hereby incorporated by reference.

The chelator can be attached to the linker arm by a number of groups. Examples of such groups, not intended for limitation, are: —O—, —NH—CO, —NH—CNH—, —N=N—, —NH—SO$_2$—, —S—, —O—PO$_2$—O—, —OSO$_2$—, —NH—N=N—, —NH—CH$_2$—, —CH$_2$—NH—, —N—, —O—CH$_2$—, O—CO—, —NH—CO—CH$_2$—S—, —NH—CO—CH$_2$—NH—, —O—CH$_2$—CH$_2$—O—, —O—CO—CH$_2$—, —S—CH$_2$—, and —O—CO—NH.

Varying conditions can be used for attaching a chelator to a linker arm. Generally, any pH range from about 4 to about 10, preferably from about 5 to about 8, any temperature from about 20° C. to about 100° C., preferably from about 40° C. to about 65° C., any solvent, and any buffer or catalyst can be used as long as the pH, temperature, solvent, or buffer does not modify any of the groups or moieties of the antigen, antibody or polynucleotide. Thus, for example, reagents or conditions that can depurinate or deaminate the polynucleotide should be avoided. There are also relatively few limitations as to reaction times. The optimum pH, temperature, solvent, or reaction time for attaching a chelator to a linker arm will depend on the linker arm, the chelator, and the functionalities to be reacted. The conditions can readily be determined by one skilled in the art.

The stoichiometry of the reactants required for these reactions can vary widely. Generally, an excess of the component that is more easily prepared will be used for the attachment of the chelator to the antigen, antibody or polynucleotide. In practice, the amounts will vary depending upon the required reaction conditions, the chelator, the linker arm, and their reacting functional groups.

The chelator can be attached to the linker arm after incorporation of the linker arm-containing nucleotide into the polynucleotide or before incorporation of the linker arm-containing nucleotide into the polynucleotide. The only limitation is that the chelator cannot be attached before incorporation if it interferes with polynucleotide synthesis.

The binding entity can comprise one chelator or more than one chelator. When the recognition segment is a polynucleotide, the chelator can be attached at terminal positions or at non-terminal positions of the polynucleotide probe. The greater the number of chelators, the more sensitive the binding entity will be. However, the chelators should not be present in such numbers that effective complexing of the analyte to the binding entity is substantially prevented. The number of chelators that can be attached will depend on the composition, the size and length of the recognition segment.

6. DESCRIPTION OF THE LANTHANIDE METAL

Certain lanthanide metal chelates fluoresce for a time period considerably longer than aromatic compounds. Two such metal chelates are europium and terbium which fluoresce for about several milliseconds. Tebium ($Tb^{+3}$) emits in the 480 to 630 nm range and europium ($Eu^{+3}$) emits in the 580 to 700 nm range. Both have long excited-state lifetimes because of the forbidden nature of the transition between their ground state and lowest excited state. The absorbance coefficients of these lanthanides are of the order of $0.1 \, M-1 \, cm^{-1}$ compared with $10^3$ to $10^5 \, M-1 \, cm^{-1}$ for most fluorescent organic detection of these metals after background fluorescence due to aromatic compounds has decayed. These metal chelates have additional advantages in that their absorbance is very strong (about 104), their excitation maximum is within the short uv range (terbium chelates are excited at 270–320 and about 488 nm, while europium chelates are excited at 320–360 and about 580 nm), their excitation maximum are independent of the complexed ligands which makes it possible to excite them with commercially available lamps or lasers, their emissions can be monitores with a narrow band width, and they have the ability to laser in different solutions and at different temperatures.

The fluorescence emission of the lanthanide metal chelates can arise from the absorption of energy by an energy absorbing species which can be a proximate ligand or aromatic compound of excitation radiation, conversion of this energy from the singlet state to the triplet state, and transfer of this energy from the energy-absorbing species to that of the metal. The energy is then emitted as by the metal fluorescence for a relatively long interval at a narrow band width and long wavelength characteristic of metals. The fluorescence of terbium green while that of europium is purple.

7. DESCRIPTION OF THE FLUORESCENT AROMATIC AGENT

The fluorescent aromatic agent can be either the $E_1$ or the $E_2$. When it is the $E_1$, it must emit fluorescence of a wavelenth that can be absorbed by the $E_2$. When it is the $E_2$, it must emit some fluorescence at a wavelength that is longer than that emitted by the $E_1$. Detection of the $E_2$ can be carried out by measuring the fluorescence with a filter that cuts off all fluoresecence emission of the $E_1$ but allows the longer wavelength fluorescence of the $E_2$ to pass through.

When both the $E_1$ and $E_2$ are fluorescent aromatic agents, any combination of agents which satisfy the criteria listed in the preceeding paragraph are satisfactory. When the $E_1$ is a fluorescent aromatic agent and the $E_2$ is a lanthanide metal, then when the analyte is a target polynucleotide, the binding entity can comprise, for example, tryptophan as the $E_1$. It has been demonstrated that tryptophan can effectively transfer energy to an $E_2$. Even a single tryptophan residue bond to a polynucleotide is an excellent $E_1$ because its emission, centered about 330 nm, overlaps the absorption of many potential energy acceptors, including the lanthanide metals. See the article by W. D. Horrocks, Jr., B. Holmquist, and B. L. Vallee in Proc. Natl. Acad. Sci. U.S.A. (1975), 72: 4763–68, which is hereby incorporated by reference. When the analyte is an antigen or an antibody, the fluorescent aromatic agent can be, for example, lumichrome, 9-aminoacridine, and auromine O.

The fluorescent aromatic agent is attached to the linker arm by means of a suitable functional group. Such methods are described hereinabove.

8. DESCRIPTION OF THE INTERCALATING AGENT

A number of fluorescent aromatic agents or dyes are able to intercalate into double-stranded polynucleotide helices. The double-strand polynucleotide can be DNA/DNA, RNA/RNA, or DNA/RNA. These agents show a shift in fluorescence emission after intercalation into a double-stranded helix. This shift is caused by a change in the hydrophobic environment of these agents.

Generally, the intercalating agents are aromatic dyes. These intercalating aromatic dyes have a planar ring structure and have distinct fluorescence emission spectra. The fluorescence is indicative of the electron delocalization of the intercalating agent, and is affected by the inductive effect of substituent groups attached to the dye and by quenching agents.

The result of intercalation is the spreading of adjacent base pairs to about twice their normal separation distance, leading to an increase in molecular length of the duplex. Further, unwinding of the double helix of about 12 to 36 degrees must occur in order to accomodate the intercalator. General reviews and further information can be obtained from Lerman, J., Mol. Biol. 3:18 (1961); Bloomfield et al, "Physical Chemistry of Nucleic Acids", Chapter 7, pp. 429–476, Harper and Rowe, New York (1974); Waring, Nature 219:1320 (1968); Hartmann et al, Angew. Chem., Engl. Ed. 7:693 (1968); Lippard, Accts. Chem. Res. 11:211 (1978); Wilson, Intercalation Chemistry (1982), 445; and Berman et al, Ann. Rev. Biophys. Bioeng. 10:87 (1981); as well as from the above-referenced U.S. Ser. No. 560,429. Exemplary of intercalators are acridine dyes, e.g., acridine orange, the phenanthridines, e.g., ethidium, anthracyclines, e.g. adriamycin, the phenazines, furocoumarins, phenothiazines, and quinolines.

9. ANALYTE

A. ANTIGENS AND ANTIBODIES

This method can be used to detect most antibodies and antigens. The antibody can be monoclonal or polyclonal. The epitope of the antigen can comprise a protein, a carbohydrate, or both. The antigen can comprise one unit or a number of subunits. The antigen can be from a microorganism, a plant cell, or a mammalian cell. The microorganism can be a bacterium, fungus, virus, or yeast. The antigen can be an epitope of the microorganism or cell, or can be a product secreted by the microorganism or cell. The antigen can be, for example, a membrane receptor, a blood cell, or a muscle protein.

B. TARGET POLYNUCLEOTIDE

This method can be used to detect a target polynucleotide, for example, from a microorganism, a plant cell, or a mammalian cell. The microorganism can be a bacterium, fungus, virus, or yeast. The target polynucleotide can be one that is unique for a particular pathogenic virus, one that is present in a mutated mammalian gene that results in the production of a non-functioning protein, or one that imparts antibiotic resistance to a bacteria. For example, it can be one that imparts penicillin resistance in *Streptococcus pyogenes* or *Neisseria meningitidis;* tetracycline resistance in *Staphylococcus aureus, Candida albicans, Pseudomonas aeruginosa, Streptococcus pyogenes,* or *Neisseria gonorrhoeae;* and aminoglycoside resistance in *Mycobacterium tuberculosis.*

C. ANALYTE SOURCE

The test sample to be assayed can be any medium of interest, and will usually be a liquid sample of medical, veterinary, environmental, nutritional, or industrial significance. Human and animal specimens and body fluids particularly can be assayed by the present method, including urine, blood (serum or plasma), amniotic fluid, milk, cerebrospinal fluid, sputum, fecal matter, lung aspirates, throat swabs, genetal swabs and exudates, rectal swabs, and nasopharyngeal aspirates. Where the test sample obtained from the patient or other source to be tested contains principally double stranded nucleic acids, such as contained in cells, the sample will be treated to denature the nucleic acids, and if necessary first to release nucleic acids from cells. Denaturation of nucleic acids is preferably accomplished by heating in boiling water or alkali treatment (e.g., 0.1 N sodium hydroxide), which if desired, can simultaneously be used to lyse cells. Also, release of nucleic acids can, for example, be obtained by mechanical disruption (freeze/thaw, abrasion, sonication), physical/chemical disruption (detergents such as Triton, Tween, sodium dodecylsulfate, alkali treatment, osmotic shock, or heat), or enzymatic lysis (lysozyme, proteinase K, pepsin). The resulting test medium will contain nucleic acids in single stranded form which can then be assayed according to the present hybridization method.

This approach can be extended to the diagnosis of genetic disorders, such as thalassemia and sickle cell anemia. The polynucleotide gene whose presence of absence (in the case of thalassemia) is associated with the disorder can be detected following hybridization with a polynucleotide probe according to this invention.

The mapping of genes or their transcripts to specific loci on chromosomes has been a tedious and time-consuming occupation, involving mainly techniques of cell-fusion and somatic cell genetics. Although in-situ hybridization has been employed successfully for mapping single-copy gene sequences in species that undergo chromosome polytenization, such as that of Drosophila, detection of unique sequence genes in most higher eukaryotic chromosomes has been extremely difficult, if not impossible, using standard hybridization methods. The necessity for polynucleotide probes of very high specific radioactivity to facilitate autoradiographic localization of the hybridization site also results in rapid radiodecomposition of the polynucleotide probe and a concomitant increase in the background noise of silver grain deposition. The use of hybridization probes with low to moderate specific radioactivities requires exposure times of many days or weeks, even to detect multicopy sequences, such as ribosomal RNA genes or satellite DNA. Since recombinant DNA technology has made feasible the molecular cloning of virtually every sngle-copy sequence found in eukaryotic cells, it would be extremely beneficial to have a rapid and sensitive method for mapping the chromosomal origin of such cloned genomic fragments.

Finally tumor cells can be diagnosed by preparing a polynucleotide probe according to this invention which is complementary to the messenger ribonucleic acid transcribed from a deoxyribonucleic acid gene sequence associated with the production of polypeptides, such as fetal protein antigen or carcinoembryonic antigen, the presence of which is diagnostic for specific tumor cells. Hybridization and detection of the probe/target polynucleotide hybrid would provide a method for detecting the tumor cells.

10. DETECTION OF DELAYED FLUORESCENCE

Figure 2:
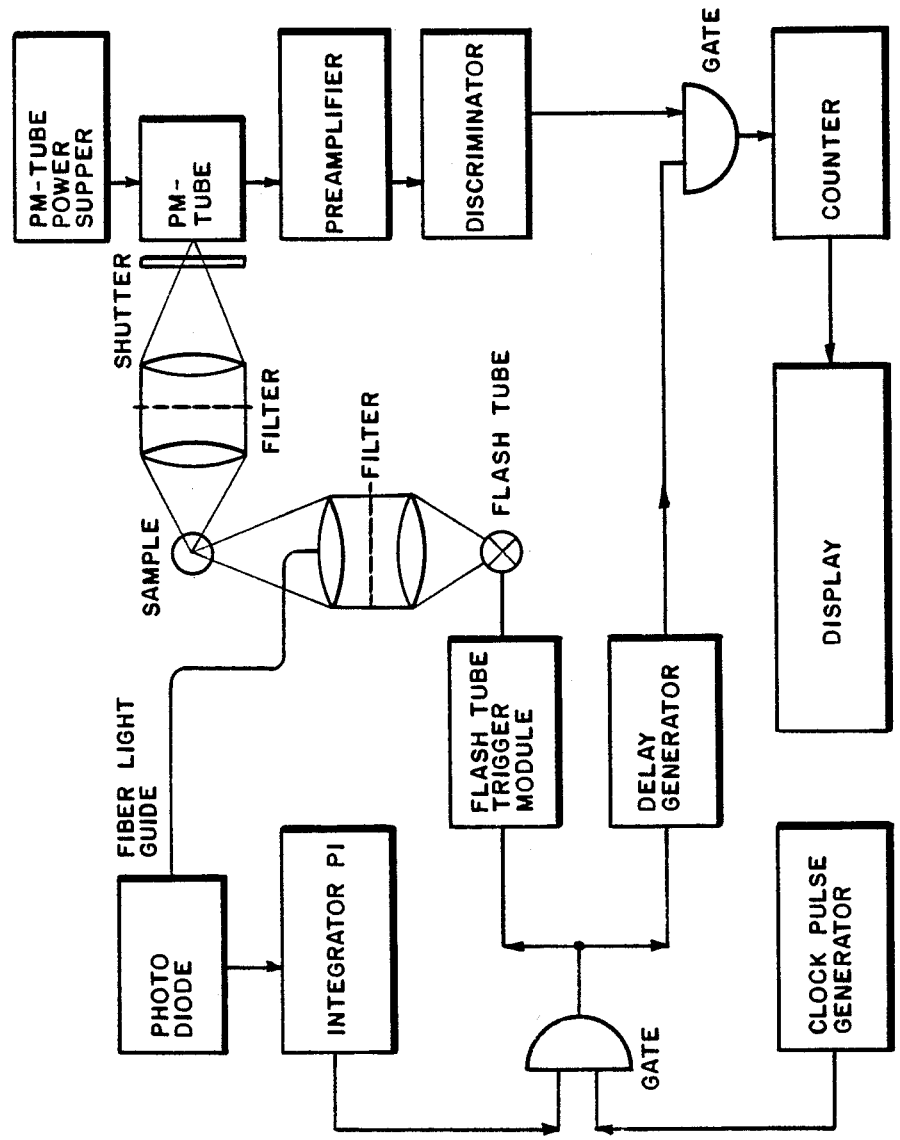
FIG. 2 shows a schematic diagram of a fluorimeter which can be used to carry out the detection of an analyte with a probe comprising a lanthanide metal.

The detection of delayed fluorescence can be measured by means of an instrument shown in FIG. 2. This instrument was developed by Erkki Soini and Hannu Kojola. See Clin. Chem. 29/1,65–68 (1983). The sample compartment is covered by a light-tight lid and the sample is changed manually. The samples are held in small disposable tubes or cuvettes made of polystyrene, which has a reasonably low long-decay background fluorescence. Because the intensity of the single flashes from the xenon flashtube was not very reproducible, we had to ensure stabilization of the excitation system. An integrator (P1) for a semiconductor photodiode serves as the stabilizer of the flash lamp. The flask lamps is activated about $10^3$ times at a frequency of 1 kHz. The exact number of flashes (N) is controlled by the integrator P1 so that the integrated intensity of the photon emission is thus fixed. For the stabilization detector we used a photodiode (Model UV-215B; EG and G Inc., Electro-optics Div., 35 Concress St., Salem, Mass. 01970), operated in the photovoltaic mode and connected to the optical system by a fiber light guide. The integrator is made of an operational amplifier, which provides a control signal for the flash tube circuit. The integrated photon emission from the flashtube is stabilized by this method with a precision of $\pm(1/N).100\%$ assuming that the deviation of the intensity of single flashes is not greater than $\pm 50\%$.

This stabilization method has many advantages. First of all, the system is simple, the flashtube and its power supply can be made without any stabilization circuit and less expensive flashtubes with lower stability can be used. The temperature dependence of the system can be minimized by a single compensator element. The flashtube is operated only during a measurement, thus ensuring a long practical life. The eventual fatigue of the flashtube will be automatically compensated by the integrator.

The pulsed-light source used in this fluorometer was an FX-198 bulb-type xenon flashtube with a 1.5-mm arc cap (EG and G Inc.). An EG and G Lite-Pac Trigger Module produced the high-voltage trigger pulses required to operate the flashtube. We operated the flashtube system at +600 V and a flash duration of 0.5 us.

To provide optimal excitation and emission bands, we used intereference band-pass filters (Ferroperm AS, Copenhagen, Denmark) mounted inside the sample compartment for easy and quick replacement.

The detector is a side-window photomultiplier tube (Model R928; Hamamatsu TV co. Ltd., 1126 Ichonocho, Hamatsu, Japan) operated with negative-bias voltage, thus obtaining a direct analog signal between the anode and ground. We found this to be a practical arrangement for monitoring the total amount of fluorescence and obtaining an indication of counter saturation.

The photomultiplier tube, operated in the single-photon mode, is connected to a fast preamplifier and discriminator and to a fast scaler having a digital display of seven decades. The counting speed of random events is limited to 40 MHz by the preamplifier and single-photon discriminator.

11. METHOD FOR DETECTING THE ANALYTE

A. THE ANALYTE IS AN ANTIBODY OR ANTIGEN

The antigen or the antibody is generally purified from circulating body fluids. In addition, the detection of the antigen may involve lysing a cell. Antigens and antibodies are generally purified using, for example, affinity columns, ammonium sulfate fractionation, in exchange chromatography, gel eletrophoresis, and immunodiffusion. The purified antigen or antibody analyte is added to a solution comprising the binding entity and the reporting entity. Alternatively, either the analyte or the binding entity is immobilized to a support and the other components are dissolved in solution. Furthermore, the reporting entity may also comprise the support. The appearance of bathochromic and/or delayed fluorescence following irradiation of the $E_1$ indicates the presence of the analyte.

B. THE ANALYTE IS A POLYNUCLEOTIDE

The target polynucleotide is generally isolated from microorganisms or cells. One method using a polynucleotide probe, wherein a lanthanide metal is the signalling segment, is carried out, for example, by lysing the cells in a sample comprising the target polynucleotide in a solution to release the target polynucleotide from the surrounding membrane. Lysis can be, for example, by exposing the sample to sonication, or to a detergent. The polynucleotides can be separated from cell debris by centrifugation, and purified further by alcohol precipitation, or by dialysis. The polynucleotide probe is then added to a solution, containing the target polynucleotide. The appearance of delayed fluorescence indicates the presence of the target polynucleotide in the sample.

The target polynucleotide must be rendered in single-stranded form during the hybridization step before it can hybridize with the polynucleotide moiety portion of the polynucleotide probe. This can be achieved either by heat or by alkali. Typically, hybridization will proceed at slightly elevated temperatures, e.g., between about 35° and 75° C. and usually at about 65° C., in a solution comprising buffer at pH between about 6 and 8 and with appropriate ionic strength (e.g., 5XSSC where 1XSSC=0.15M sodium chloride and 0.015M sodium citrate, pH 7.0). In cases where lower hybridization temperatures are desirable, hydrogen bonding reagents such as dimethyl sulfoxide and formamide can be included. The degree of complementarity between the sample and probe strands required for hybridization to occur depends on the stringency of the conditions. Factors which determine stringency are known in the art.

Following hybridization, the solution is placed in an instrument in which the aromatic agent is excited with photons of the proper wavelength. The fluorescence emission is then measured after a predetermined time interval which can vary between 4-6 milliseconds.

The polynucleotide probe has attached to it at least one chelator. A lanthanide metal, for example, terbium, is complexed to the chelator. The metal has the ability to absorb energy emitted at particular wavelengths by selective fluorescent aromatic agents and furthermore has the ability to emit fluoresence for time periods substantially longer than that of the aromatic agents themselves. The presence of the target polynucleotide is thus determined by contacting the sample suspected of containing the target polynucleotide with (1) the polynucleotide probe to which the chelator is covalently bound and which also comprises a terbium complexed to the chelator and (2) a fluorescent aromatic intercalating agent which emits fluorescent energy capable of being absorbed by the terbium. The emission of fluorescence at a longer wavelength than that emitted by the intercalating agent or of fluorescence after a given interval during which the fluorescence of the intercalating agent has decayed indicates the presence of the target polynucleotide.

This assay, by detecting a target polynucleotide in one step, avoids many limitations of other detection assays. For example, since there is no need to remove unbound probe molecules, there is no requirement that the hybridization must withstand various conditions or manipulations, such as elevated temperatures, phenol and organic solvent extractions, electrophoresis, column chromotography or low or high pH.

12. REAGENT KITS

The present invention additionally provides a reagent kit, i.e., reagent combination or means, comprising all of the essential elements required to conduct a desired assay method. The reagent system is presented in a commercially packaged form, as a composition or admixture where the compatibility of the reagents will allow, in a test kit, i.e., a packaged combination of one or more containers, devices, or the like holding the necessary reagents, and usually including written instructions for the performance of assays. Reagent systems of the present invention include all configurations and compositions for performing the various complexing or hybridization formats described herein.

The reagent system will generally comprise (1) a binding entity and a reporting entity. A test kit form of the system for target polynucleotides, for example, can additionally include ancillary chemicals such as the components of the hybridization solution and denaturation agents capable of converting double stranded nucleic acids in a test sample into single stranded form. Preferably, there is included a chemical lysing and denaturing agent, e.g., alkali, for treating the sample to release single stranded nucleic acid therefrom.

Although assays for the detection of several analytes have been described hereinabove, the assays can be used for the detection of other analytes using appropriate binding entities. Examples of various analyte/binding entity combinations include, but are not limited to, lectin/sugar; sugar/lectin; hormone/receptor; receptor/hormone; inhibitor/enzyme; enzyme/inhibitor; cofactor/enzyme; enzyme/cofactor; ligand/substrate; and substrate/ligand. It is intended that these combinations be included within the scope of the inventions.

We claim:

1. An assay for detecting the presence of an analyte comprising the steps of:
    a. forming a complex comprising said analyte and binding entity comprising an analyte recognition segment and a first partner of a fluorescent energy transfer system, wherein said first partner is selected from the group consisting of an energy donor and an energy acceptor, wherein said energy donor is a fluorescent aromatic agent or a lanthanide metal and said energy acceptor is a fluorescent, aromatic agent or a lanthanide metal, with the proviso that when said energy donor is a fluorescent, aromatic agent, then said energy acceptor is a fluorescent, aromatic agent or a lanthanide metal and when said energy donor is a lanthanide metal, then said energy acceptor is a fluorescent, aromatic agent;

b. contacting said complex with a reporting entity composition comprising a second partner of said fluorescent energy transfer system and at least one component for rendering said analyte detectable which binds to said second partner to form a unit, wherein: (i) said second partner is selected from the group consisting of an energy donor and an energy acceptor, with the proviso that when said first partner is an energy donor then said second partner is an energy acceptor and when said first partner is an energy acceptor then said second partner is an energy donor, and (ii) the distance between said first partner and said second partner is 30 Angstroms or less;

c. irradiating said unit with energy that can be absorbed by said energy donor and not by said energy acceptor with the proviso that said energy donor emits fluorescent energy which can excite said energy acceptor; and d. detecting the fluorescence emitted by said energy acceptor.

2. The method of claim 1 wherein said first partner is attached covalently to said recognition segment of said binding entity by means of a linker arm.

3. The method of claim 1 wherein said binding entity comprises an analyte-specific binding substance, said first partner is selected from the group consisting of europium and terbium, and said second partner is a fluorescent aromatic intercalating agent.

4. The method of claim 1 wherein said lanthanide metal is chelated.

5. The method of claim 1 wherein said assay is carried out in a one phase system.

6. The method of claim 1 wherein said analyte is selected from the group consisting of antigens, haptens, antibodies and target polynucleotides.

7. The method of claim 6 wherein said analyte is an antigen.

8. The method of claim 7 wherein said antigen is selected from the group consisting of proteins, polysaccharides, viruses, phages, and bacteria.

9. The method of claim 1 wherein said first partner is an energy acceptor and said second partner is an energy donor.

10. The method of claim 1 wherein said energy donor is a fluorescent aromatic agent and said energy acceptor is selected from the group consisting of fluorescent aromatic agents and lanthanide metals.

11. The method of claim 10 wherein said energy donor is a fluorescent aromatic agent and said energy acceptor is a lanthanide metal.

12. The method of claim 1 wherein aromatic agents are selected from the group consisting of auromine O, lumichrome, and 9-aminoacridine.

13. The method of claim 10 wherein said metal is selected from the group consisting of europium and terbium.

14. The method of claim 1 wherein said second partner is attached covalently or non-covalently to said component of said reporting entity by means of a linker arm.

15. The method of claim 6 wherein said analyte is selected from the group consisting of antigens and antibodies and wherein said component of said reporting entity is selected from the group consisting of Clq, antibodies, and solid supports.

16. The method of claim 15 wherein said analyte is selected from the group consisting of antigens and antibodies and wherein said component of said reporting entity is selected from the group consisting of Clq and solid supports.

17. The method of claim 6 wherein said analyte is a target polynucleotide and wherein said component of said reporting entity is selected from the group consisting of intercalating agents and solid supports.

18. The method of claim 3 wherein said solid support is selected from the group consisting of glass, plastic, cellulose, and gel polymers.

19. The method of claim 1 wherein said assay is carried out in a two phase system, wherein said two phases comprise a solid support and a liquid.

20. The method of claim 1 wherein said analyte is an antigen, said first partner is an energy acceptor, said second partner is an energy donor, and said component of said reporting entity selected from Clq and a solid support.

21. The method of claim 20 wherein said energy acceptor is a lanthanide metal.

22. The method of claim 5 wherein said analyte is an antigen, said binding entity comprises an antibody said first partner is an energy acceptor, said second partner is an energy donor, and said reporting component entity comprises Clq.

23. The method of claim 22 wherein said energy acceptor is a lanthanide metal.

24. The method of claim 1 wherein said analyte is a target polynucleotide, said recognition segment is a complementary polynucleotide, said first partner is a lanthanide metal, and said second partner is a fluorescent aromatic intercalating agent.

25. The method of claim 5 wherein said analyte is a target polynucleotide, said binding entity comprises a complementary polynucleotide, said first partner is a lanthanide metal, and said second partner is a fluorescent aromatic intercalating agent.

26. The method of claim 19 wherein said analyte is a target polynucleotide, said binding entity comprises a complementary polynucleotide, said first partner is a lanthanide metal, said second partner is a fluorescent aromatic intercalating agent.

27. The method of claim 1 wherein said analyte and said binding entity form a complex selected from the group consisting of antigen/antibody, lectin/sugar, hormone/receptor, inhibitor/enzyme, cofactor/enzyme, and ligand/substrate.

28. The method of claim 5 wherein said analyte is an antigen and wherein said binding entity comprises a specific antibody.

29. An assay for detecting the presence of an analyte comprising the steps of:

a. forming a complex comprising said analyte and a binding entity comprising an analyte recognition segment and a first partner of a fluorescent energy transfer system, wherein said first partner is selected from the group consisting of an energy donor and an energy acceptor, wherein said energy donor is a fluorescent, aromatic agent and said energy acceptor is selected from the group consisting of fluorescent, aromatic agents, europium and terbium;

b. contacting said complex with a reporting entity comprising a second partner of said fluorescent energy transfer system and a component which binds to said second partner to form a unit, wherein: (i) said second partner is selected from the group consisting of an energy donor and an energy acceptor, with the proviso that when said first partner is an energy donor then said second partner is an energy acceptor and when said first partner is an energy acceptor then said second partner is an energy donor, and (ii) the distance between said first partner and said second partner is 30 Angstroms or less;

c. irradiating said unit with energy that can be absorbed by said energy donor and not by said energy acceptor with the proviso that said energy donor emits fluorescent energy which can excite said energy acceptor and wherein said irradiation is performed without prior separation of said binding entity which has not formed said complex with said analyte; and d. detecting the fluorescence emitted by said energy acceptor.

30. The method of claim 29 wherein said binding entity comprises an analyte-specific binding substance, said first partner is selected from the group consisting of europium and terbium, and said second partner is a fluorescent aromatic intercalating agent.

31. The method of claim 29 wherein said assay is carried out in a two phase system, wherein said two phases comprise a solid support and a liquid.

32. The method of claim 29 wherein said europium is chelated.

33. The method of claim 29 wherein said terbium is chelated.

34. The method of claim 29 wherein said assay is carried out in a one phase system.

* * * * *